US012151034B2

(12) United States Patent
Richards et al.

(10) Patent No.: US 12,151,034 B2
(45) Date of Patent: *Nov. 26, 2024

(54) BIODEGRADABLE ABSORBENT ARTICLES

(71) Applicant: Everyone's Earth Inc., Ossining, NY (US)

(72) Inventors: Nicole M. Richards, Madison, CT (US); Thomas C. Kallish, Ossining, NY (US)

(73) Assignee: Everyone's Earth Inc., Bedford Hills, NY (US)

( * ) Notice: Subject to any disclaimer, the term of this patent is extended or adjusted under 35 U.S.C. 154(b) by 486 days.

This patent is subject to a terminal disclaimer.

(21) Appl. No.: 16/908,621

(22) Filed: Jun. 22, 2020

(65) Prior Publication Data

US 2020/0316245 A1    Oct. 8, 2020

Related U.S. Application Data

(63) Continuation of application No. 15/211,819, filed on Jul. 15, 2016, now Pat. No. 10,709,806.

(Continued)

(51) Int. Cl.
*A61F 13/15* (2006.01)
*A61F 13/511* (2006.01)
(Continued)

(52) U.S. Cl.
CPC ........ *A61L 15/46* (2013.01); *A61F 13/15252* (2013.01); *A61F 13/51104* (2013.01); *A61F 13/51121* (2013.01); *A61F 13/51405* (2013.01); *A61F 13/534* (2013.01); *A61F 13/53409* (2013.01); *A61F 13/538* (2013.01);
(Continued)

(58) Field of Classification Search
CPC ........ A61L 15/46; A61L 15/225; A61L 15/42; A61L 15/60; A61L 15/62; A61F 13/51104; A61F 13/51121; A61F 13/51405; A61F 13/534; A61F 13/53409; A61F 13/538; A61F 13/5633; A61F 13/8405; A61F 2013/15016; A61F 2013/530255; A61F 2013/530343; A61F 2013/53035; A61F 2013/530379; A61F 2013/530496; A61F 2013/8426
See application file for complete search history.

(56) References Cited

U.S. PATENT DOCUMENTS

| 5,300,358 | A * | 4/1994 | Evers | A61L 15/24 604/382 |
| 6,713,414 | B1 * | 3/2004 | Pomplun | C11D 3/046 428/913 |

(Continued)

*Primary Examiner* — Jacqueline F Stephens
(74) *Attorney, Agent, or Firm* — Murtha Cullina, LLP

(57) ABSTRACT

A biodegradable, disposable absorbent article, such as a diaper, having a non-woven inner layer of natural fibers and a non-woven outer layer of natural fibers and a treatment applied to at least one surface thereof. The treatment includes at least one compound selected from the group consisting of waxes, urethanes, silicones, fluorocarbons, and non-fluorochemical repellants. The absorbent article has a core of natural fibers or fibrous material, and optionally polyacrylate superabsorbent particles, positioned between the inner layer and the outer layer. The article may contain polylactic acid films between the layers.

20 Claims, 7 Drawing Sheets

Related U.S. Application Data

(60) Provisional application No. 62/295,678, filed on Feb. 16, 2016, provisional application No. 62/195,498, filed on Jul. 22, 2015.

(51) Int. Cl.
| | |
|---|---|
| *A61F 13/514* | (2006.01) |
| *A61F 13/534* | (2006.01) |
| *A61F 13/538* | (2006.01) |
| *A61F 13/56* | (2006.01) |
| *A61F 13/84* | (2006.01) |
| *A61L 15/22* | (2006.01) |
| *A61L 15/42* | (2006.01) |
| *A61L 15/46* | (2006.01) |
| *A61L 15/60* | (2006.01) |
| *A61L 15/62* | (2006.01) |
| *A61F 13/53* | (2006.01) |

(52) U.S. Cl.
CPC ...... *A61F 13/5633* (2013.01); *A61F 13/8405* (2013.01); *A61L 15/225* (2013.01); *A61L 15/42* (2013.01); *A61L 15/60* (2013.01); *A61L 15/62* (2013.01); *A61F 2013/15016* (2013.01); *A61F 2013/530255* (2013.01); *A61F 2013/530343* (2013.01); *A61F 2013/53035* (2013.01); *A61F 2013/530379* (2013.01); *A61F 2013/530496* (2013.01); *A61F 2013/8426* (2013.01)

(56) References Cited

U.S. PATENT DOCUMENTS

| | | | |
|---|---|---|---|
| 10,709,806 B2 * | 7/2020 | Richards | A61F 13/15252 |
| 2005/0282456 A1 * | 12/2005 | Zhao | D04H 1/587 |
| | | | 604/366 |
| 2011/0092933 A1 * | 4/2011 | Canales Espinosa de los Monteros | A61L 15/62 |
| | | | 604/377 |

* cited by examiner

BIODEGRADABLE ABSORBENT ARTICLES

CROSS REFERENCE TO RELATED APPLICATION

The instant application is a continuation application of, and claims priority benefit to, co-pending U.S. patent application Ser. No. 15/211,819 entitled "Biodegradable Absorbent Articles filed on Jul. 16, 2016, which claims priority to U.S. Provisional Application No. 62/295,678 filed on Feb. 16, 2016 and U.S. Provisional Application No. 62/195,498 filed on Jul. 22, 2015. The entireties of each of the aforementioned patent applications are incorporated herein by reference.

FIELD OF THE INVENTION

The present invention relates to fluid-absorbing structures (absorbent articles), such as diapers, incontinence products, feminine hygiene products, etc., and more particularly, relates to biodegradable, disposable absorbent articles, such as diapers, incontinence products and feminine hygiene product, that are formed primarily of natural fibers, e.g., cotton, and thus represent an eco-friendly (biodegradable) product.

BACKGROUND OF THE INVENTION

Articles used to absorb waste body fluids such as urine, blood, menses, and the like, are used in large quantities worldwide. These articles are commonly referred to as being "absorbent articles". Typically, these articles are in the form of diapers, and other like products, such as, feminine hygiene products and incontinence products, which have become increasingly popular as a modern convenience and necessity.

Absorbent articles in the form of diapers generally come in two varieties, namely, reusable cloth diapers and disposable diapers. Modern cloth diapers come with liners, including flushable liners, which hold the waste and permit disposal into a toilet or the like. Disposable diapers greatly increased in popularity following the introduction of superabsorbent polymers (SAP) in diapers in the mid-80s and today, an estimated 90% of U.S. parents use disposable diapers.

A basic disposable diaper includes the following components: (a) an inner layer or top sheet that sits next to the baby's skin and thus, serves as the initial layer that contacts waste fluids; (b) an absorbent core that absorbs and holds the fluids (most absorbent cores are made of fluff made from wood pulp fibers or corn/wheat based materials and include crystals (SAP) that are dispersed throughout the fluff such that the fluff serves to distribute the fluid, while the SAP is intended to absorb the fluid and lock it in the core away from the baby); and (c) a waterproof outer shell or layer (back sheet) that provides a waterproof coating/layer (this layer is most often made of some kind of petroleum-based plastic or plastic-treated material; however, some green diaper companies are using plant-based plastic (aka bioplastic) to provide this layer). The top sheet is most commonly prepared from woven, nonwoven, or porous formed-film polyethylene or polypropylene materials. Back sheet materials typically comprise flexible polyethylene sheets along with the film barrier. The back sheet can be formed as the same material as the top sheet; however, the back sheet includes the film barrier (that acts as a fluid barrier for leak proofing the diaper) on the inner surface of the back sheet. The outer surface of the back sheet comprises the back sheet material (e.g., nonwoven polyethylene) which is soft to the touch and the film barrier is concealed in a traditional diaper construction.

Due to the widespread use of disposable diapers, large quantities of disposable infant diapers are used each year and disposal of these products is a problem. Most of the commercially available disposable diapers consist largely of plastics based on polypropylene and polyethylene which do not break down in the environment, that is they resist biodegradation totally.

In fact, the average disposable diaper can take 500 years to decompose and contains petroleum, plastics, perfumes, wood pulp, and dioxins.

In particular, in many if not most disposable diapers, the liquid permeable surface material and the leak-proof backing material are not biodegradable, although the liquid absorbing material made of fluffed pulp exhibits biodegradability. Consequently, when the diaper is disposed into the ground, the surface material and the backing material remain without being degraded. For the purpose of complete disposal, therefore, it has been necessary to burn the whole diaper or to separate the liquid-permeable surface material and the leak-proof backing material from the top sheet layer for separate disposal.

A further difficulty associated with prior art disposable diapers is that due to the large percentages of toxic chemicals in these products, rashes and skin allergies often arise in the user. Due to the requirements to maximize the absorbency of these products, the quantities of added toxic chemicals have been increased, further compounding the associated problems Biodegradability and odor is an issue with the nonwovens industry, specifically for diapers, incontinence and feminine hygiene markets. Since the absorbent articles by nature are designed to absorb and contain waste, one of the issues faced with using such products is unpleasant odors emanating from such products after they have become soiled. Odor control in absorbent products has been under investigation for many years. Many body fluids have an unpleasant odor, or develop such odors when in contact with air and/or bacteria for prolonged periods. There is therefore a perceived need to create an improved odor control agent that can be effectively incorporated into an absorbent article.

Other absorbent articles, such as feminine hygiene products and incontinence products, have similar constructions as the disposable diaper described above. There are no products currently on the market that meet the needs of those markets with non-antimicrobial protection.

Even though, a typical disposable diaper, for example, consists of a substantial amount of biodegradable materials, e.g., wood pulp fibers, and the like, there is a need for reducing the amount of non-biodegradable materials in disposable absorbent articles. There is a particular need to replace polyethylene back sheets in absorbent articles with liquid impervious films comprised of biodegradable materials, because the back sheet is typically the largest non-biodegradable component of an absorbent article.

There is further a need to replace odor absorbing materials with those made of natural and/or biodegradable materials.

WO 2016/023016 A1 discloses a disposable diaper that is biobased and/or biodegradable. The diaper is comprised of a biobased and/or biodegradable outer sheet impermeable to aqueous medium, a biobased and/or biodegradable inner sheet permeable to aqueous medium, and absorbent pad made of natural fibers and biobased superabsorbents, and biobased and/or biodegradable side sheets, fastening tabs and elastic waist strip. In particular, the outer sheet, inner sheet, side sheets, fastening tabs and fastening mat are said to be made of a thermoplastic polymer selected from the group consisting of aliphatic polyester, aromatic polyester, cellulosic fiber, nonwoven material and combinations thereof. Superabsorbents can be cellulosic based, starch based or protein based.

Biobased superabsorbent such as the cellulosic based, starch based or protein based absorbents taught in WO 2016/023016 A1 tend to clump and do not hold moisture as well as other materials that are not considered as biobased, but are still biodegradable. Further, an issue with certain thermoplastic polyesters and cellulosic fibers, such as those disclosed in WO 2016/023016 A1, is that they do not degrade in all conditions. Accordingly, use of these materials in a natural fiber containing diaper makes it difficult, if not impossible, for them to pass biodegradability tests such as ASTM Test Method 05511-12, ASTM Test Method 5338.92 or ISO CD Test Method 14855. Applicant is unaware of any diaper products actually able to pass any of ASTM D5511-12, ASTM Test Method 5338.92 or ISO CD Test Method 14855.

What is desired, therefore, are biodegradable absorbent structures that can degrade in conditions in which oxygen is, or is not, present, i.e. both aerobic an anaerobic conditions. What is also desired is a diaper comprised entirely or substantially of biodegradable materials that is compostable and/or will degrade in a landfill. In particular, it is desired to have absorbent articles that are able to pass at least one of ASTM Test Method D5511-12, ASTM Test Method 5338.92 and ISO CD Test Method 14855. It is further desired that a disposable diaper is able to pass at least one of ASTM Test Method D5511-12, ASTM Test Method 5338.92 and ISO CD Test Method 14855. It is further desired that such absorbent articles and diapers contain odor absorbing materials made of natural and/or biodegradable materials. It is also desired that any such diaper have an outer layer that is impermeable to fluids yet has soft hand feel on its outward facing surface.

SUMMARY OF THE INVENTION

It is therefore an objective of the invention to provide a biodegradable absorbent article that is comprised substantially of biodegradable materials that will degrade in a landfill and/or through composting. It is an object of the invention to provide absorbent articles that are able to pass ASTM Test Method D5511-12, ASTM Test Method 5338.92 and/or ISO CD Test Method 14855.

It is further object of the invention that the biodegradable absorbent articles are comprised of materials that degrade with and without oxygen.

It is particularly an object of the invention to provide biodegradable diapers that are able to pass at least one of ASTM Test Method 05511-12, ASTM Test Method 5338.92 or ISO CD Test Method 14855.

It is an object of the invention that biodegradable diapers have an outer layer that is impermeable to fluids yet has soft hand feel on its outer surface.

It is further an object of the invention to provide biodegradable absorbent articles, and in particular diapers, having odor absorbing materials made of natural and/or biodegradable materials.

In order to overcome the deficiencies of the prior art and to achieve at least some of the objects and advantages listed, the invention comprises a disposable absorbent article including a non-woven inner layer comprising natural fibers, a non-woven outer layer comprising natural fibers and a treatment comprising at least one compound selected from the group consisting of waxes, urethanes, silicones, fluorocarbons, non-fluorochemical repellants applied to at least one surface thereof, and a core comprising natural fibers or fibrous material positioned between the inner layer and the outer layer. The absorbent article may be a diaper, nappy, absorbent underpants, training pants, adult incontinence product, pet incontinence product, feminine hygiene product, wound dressing, or breast pad.

In some cases, the core comprises superabsorbent particles (SAP). In certain preferred embodiments, the SAP is a polyacrylate.

In certain cases, the treatment is applied to the outer layer at 100% to 200% by weight add on. In certain advantageous embodiments treatment is applied at about 125% by weight add on. In some embodiments, the hydrophobic treatment is applied only to the top surface of the outer layer. In certain other embodiments, the treatment is applied to the bottom and top surface of the outer layer.

In certain embodiments, the absorbent article further comprises an acquisition/distribution (AOL) layer between the inner layer and the core. In some of those embodiments, the AOL is comprised of polylactic acid.

In some embodiments, the core comprises a corrugated structure defined by a plurality of peaks and valleys. In certain embodiments, the core comprises a non-woven wrap surrounding loose fibers.

In certain preferred embodiments, the outer layer of the absorbent article is treated with a dendrimer wax. In some of those embodiments, the treatment is applied to a top surface of the outer layer. In some embodiments, the treatment is applied to a top and a bottom surface of the outer layer.

In certain embodiments of the absorbent article, the inner layer includes a plurality of pores.

In some cases, at least one layer of the absorbent article includes a deodorizing composition comprising between about 0.1% and about 10% of a zinc, copper, silver or aluminum salt. In some of those embodiments, the absorbent article comprises about 0.1% and about 10% zinc rincinoleate. In certain of those embodiments, the composition further comprises at least one compound selected from the group consisting of ethoxylated alcohols, ethoxylated glycols, ethoxylated oils, polymers or co-polymers of acrylic acid and combinations thereof and at least one drying agent selected from the group consisting of primary, secondary, and tertiary alcohols and combinations thereof.

In some embodiments, the absorbent article is biodegradable in that it passes at least one of ASTM Test Method 05511-12, ASTM Test Method 5338-15, and ISO CD Test Method 14855-1:2012.

The invention also comprises a biodegradable diaper comprising a non-woven inner layer comprising cotton, an outer layer comprising cotton treated with a hydrophobic agent selected from the group consisting of waxes, urethanes, silicones, fluorocarbons, and non-fluorochemical repellants and combinations thereof, and an absorbent core comprising cotton and a polyacrylate superabsorbent particles positioned between the inner layer and the outer layer.

In some embodiments, the inner layer of the diaper comprises a plurality of pores.

In certain advantageous embodiments, the diaper further comprises a polylactic acid film disposed between at least one of the core and the outer layer or the core and the inner layer. In some of those embodiments, a PLA film is disposed between both the inner layer and the core and the outer layer and the core. In other of those embodiments, a PLA film is disposed between the outer layer and the core.

In some cases, the diaper has a treatment consisting of dendrimer wax applied to the outer layer. In certain of those cases, the treatment is applied to the outer layer at 100% to 200% by weight add on. In certain advantageous embodiments the dendrimer wax is applied at about 125% by weight add on. In some embodiments, the hydrophobic treatment is applied only to the top surface of the outer layer.

In certain embodiments, the diaper further comprises a pair of lateral flaps extending from a rear portion of the outer layer, said flaps including polylactic acid hook fasteners capable of affixing the flaps to loops on a front portion of the outer layer.

In some embodiments, the diaper is biodegradable in that it passes at least one of ASTM Test Method 05511-12, ASTM Test Method 5338-15, and ISO CD Test Method 14855-1:2012.

Other objects of the invention and its particular features and advantages will become more apparent from consideration of the following drawings and accompanying detailed description.

DETAILED DESCRIPTION OF THE INVENTION

Figure 1:
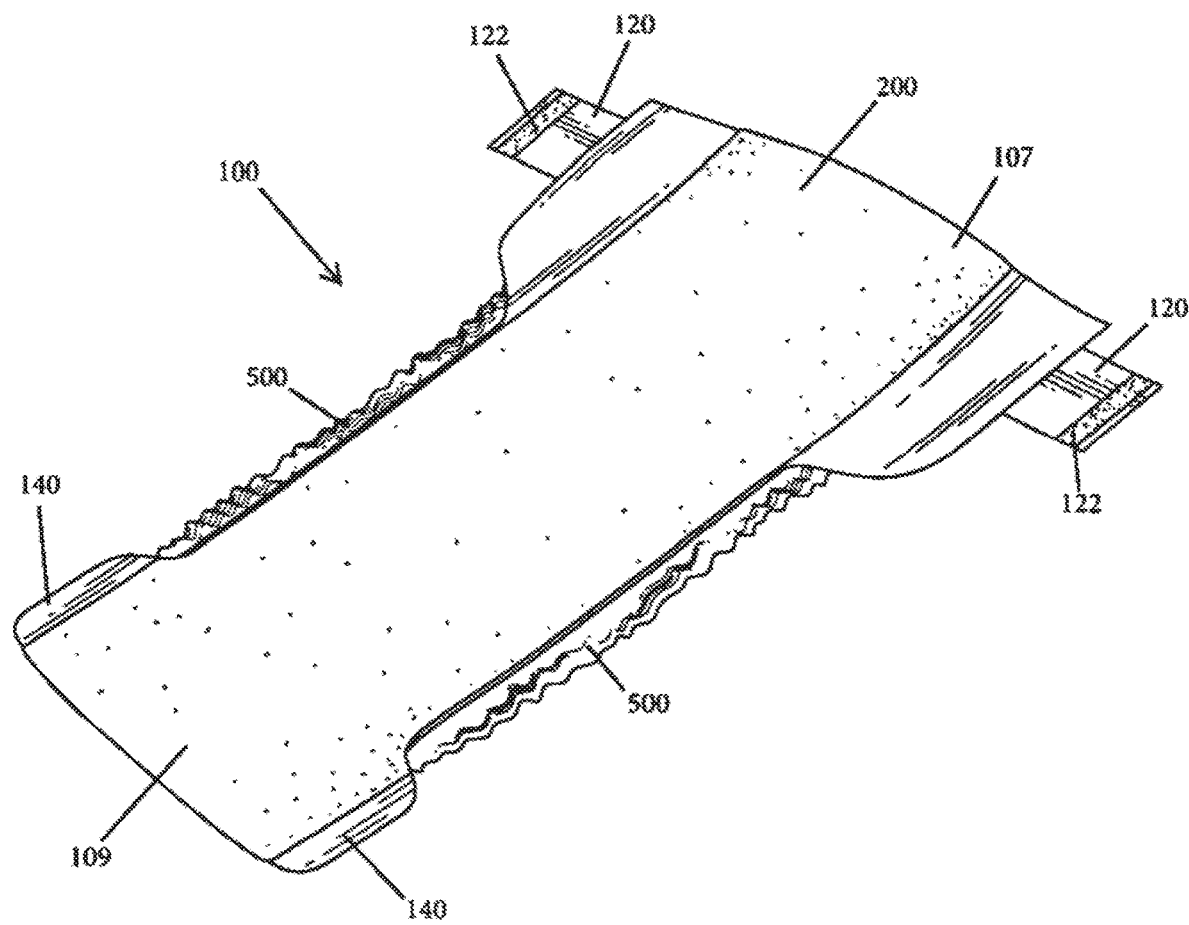
FIG. 1 is a perspective view of an absorbent article in the form of a diaper made in accordance with the present invention.

The following definitions and methods are provided to better define the present disclosure and to guide those of ordinary skill in the art in the practice of the present disclosure. Unless otherwise noted, terms are to be understood according to conventional usage by those of ordinary skill in the relevant art.

As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

As used herein the term "nonwoven" fabric or web means a web having a structure of individual fibers or threads which are interlaid, but not in an identifiable manner as in a knitted or woven fabric. Nonwoven fabrics or webs can be formed by various processes including, but not limited to, meltblowing processes, spunbonding processes, spunlacing processes and bonded carded web processes.

As used herein the term "spunbond fibers" refers to small diameter fibers of mechanically and/or eductively drawn polymeric material. Spunbond fibers are generally formed by extruding molten thermoplastic material as filaments from a plurality of fine capillaries of a spinneret with the diameter of the extruded filaments then being rapidly reduced. Examples of spunbond fibers and methods of making the same are described in, by way of example only, U.S. Pat. No. 4,340,563 to Appel et al., U.S. Pat. No. 5,382,400 to Pike et al., and U.S. Pat. No. 5,795,926 to Pike et al.; the entire content of the aforesaid patents is hereby incorporated by reference herein. Spunbond fibers are generally not tacky when they are deposited onto a collecting surface and are continuous.

As used herein "spunlaced fibers" refers to those made by a process involving the cohesion and the interlacing of ttle elementary fibers with one another is by means of a plurality of jets of water under pressure passing through a moving fleece or cloth and causing the fibres to intermingle with one another. As an example, a process for the production of spunlaced nonwoven cloths has been described in U.S. Pat. Nos. 3,214,819, 3,485,706 and 3,508,308; the entire content of the aforesaid patents is hereby incorporated by reference herein.

As used herein the term "meltblown fibers" means fibers of polymeric material which are generally formed by extruding a molten thermoplastic material through a plurality of die capillaries as molten threads or filaments into converging high velocity air streams which attenuate the filaments of molten thermoplastic material to reduce their diameter. Thereafter, the meltblown fibers can be carried by the high velocity gas stream and are deposited on a collecting surface to form a web of randomly dispersed meltblown fibers. Meltblowing processes are disclosed in, by way of example only, in U.S. Pat. No. 5,271,883 to Timmons et al.; U.S. Pat. No. 5,160,746 to Dodge et al.; U.S. Pat. No. 4,526,733 to Lau; U.S. Pat. No. 5,652,048 to Haynes et al.; and U.S. Pat. No. 5,366,793 to Fitts et al.; the entire contents of the aforesaid patents are hereby incorporated by reference herein. Meltblown fibers are generally smaller than about 10 micrometers in average diameter and, unlike spunbond fibers, are generally tacky when deposited onto a collecting surface, thereby bonding to one another during the deposition step.

As used herein the term "biodegradable" is meant to represent that a material degrades from the action of naturally occurring microorganisms such as bacteria, fungi, and algae. The biodegradability of a material may be determined using ASTM Test Method 05511-12 for anaerobic biodegradation of plastic material in high-solids anaerobic conditions, ASTM Test Method 5338-15 for aerobic biodegradation of plastic materials under controlled composting conditions, or ISO CD Test Method 14855-1:2012 or other suitable and applicable standards. The contents of ASTM Test Method D5511-12, ASTM Test Method 5338.92 and ISO CD Test Method 14855-1:2012 are incorporated herein in their entirety by reference.

The word "disposable" is used in the specification to describe absorbent articles that are not intended to be laundered or otherwise restored or reused as an absorbent article. They are intended to be discarded after a single use and preferably to be disposed of in an environmentally friendly manner.

The phrase "personal product" is intended to include products or articles used to absorb waste body fluids or other body waste, and includes diapers, nappies, absorbent underpants, training pants, adult incontinence products, pet incontinence products, feminine hygiene products, wound dressings, and breast pads. It will be appreciated that the above list is not limiting and the teachings of the present invention can be implemented into other types of absorbent products that are intended for fluid absorption.

Figure 3:
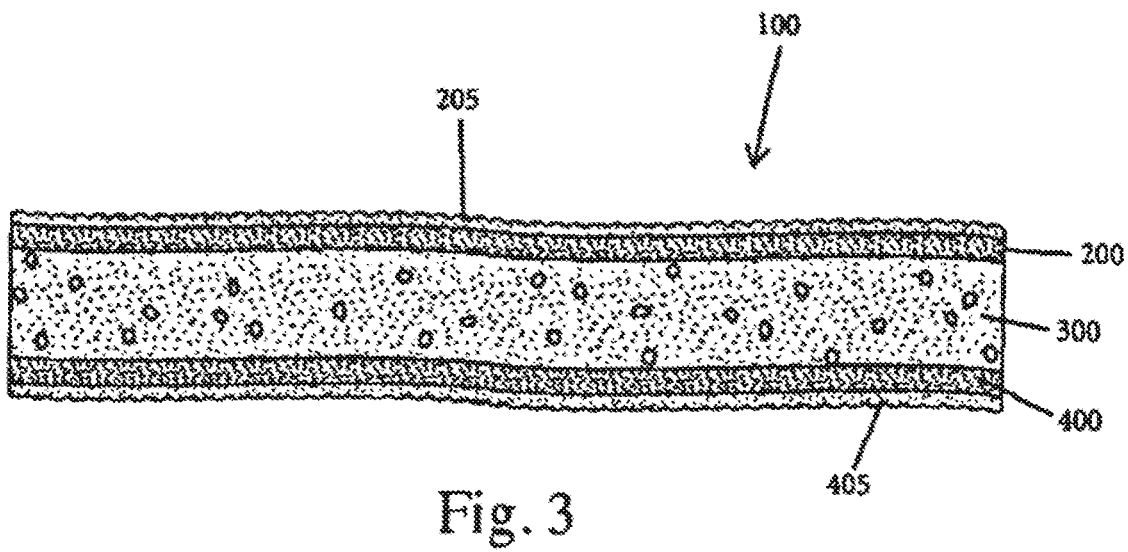
FIG. 3 is a cross-sectional view of a diaper according to a first embodiment.

FIGS. 1 and 3 illustrate an absorbent article (personal product) 100 according to one exemplary embodiment and, in particular, the absorbent article 100 is in the form of a disposable diaper for an infant (baby). It will be understood that the illustrated diaper 100 is only an exemplary embodiment and the teachings of the present invention can be implemented in a toddler training pant/diaper or other similar absorbent products, as well as the other absorbent products mentioned herein. FIG. 1 is a perspective view of the diaper 100, while FIG. 3 is a cross-sectional view of the diaper 100.

The diaper 100 is formed generally of an inner layer (top sheet) 200, an inner acquisition/distribution layer and/or absorbent core 300 and an outer shell or cover (back sheet) 400.

Inner Layer

As previously mentioned, the inner layer 200 plays an important role in the construction of the diaper since the inner layer 200 is the layer that is next to the most sensitive area of the baby's body, sometimes for hours at a time. The quality and makeup of the inner layer 200 layer also determines the level of absorbency and comfort (softness) for the baby.

In accordance with the present invention, the inner layer 200 is formed from natural fibers (e.g., 100% organic, natural cellulosic fibers). More specifically, the inner layer 200 comprises a non-woven fabric (material) that is formed from natural fibers. Any number of different natural fibers can be used to form the non-woven inner layer 200 so long as they are suitable for the intended use described herein. Exemplary natural fibers, include but are not limited to, both plant-based natural fibers and animal-based natural fibers. Plant-based natural fibers include, but are not limited to, cotton, hemp, flax, ramie, bamboo, etc.

Cotton is the most widely used natural fiber and is very absorbent, easy to care for, and comfortable for babies. Cotton is almost pure cellulose and is both soft to the touch and advantageously has breathability. As with many materials, cotton is available and marketed in an organic form which is generally understood to mean that the cotton is grown from non-genetically modified plants without the use of any synthetic agricultural chemicals, such as fertilizers or pesticides.

Hemp fiber comes from the plant species *Cannabis sativa*. Hemp is not typically certified organic, but its production is considered organic by definition. Hemp grows quickly and does not require the use of fertilizer or pesticides. When used in diapers, hemp is quite absorbent, thick, and durable.

Bamboo is a sustainable crop; its quick growth allows it to be replaced quickly with a new crop. Like hemp, it does not typically require fertilizers or pesticides to grow. Bamboo is nice for diapering because it is soft and very absorbent.

Animal-based natural fibers include, but are not limited to, wool. As described herein, wool is more particularly suited as a material to form the outer shell (back sheet) 400 since wool-based covers work very well at containing leaks and allowing air to circulate. Organic wool contains no pesticide residue and the sheep are raised organically.

In addition, rayon (e.g., viscose rayon), which is a natural-based material made from the cellulose of wood pulp, is also suitable as the inner layer material.

In addition, the inner layer 200 can be formed from biopolymers which are biodegradable. For example, polylactide biopolymers offer a renewable and biodegradable or recyclable alternative to petrochemical-based fibers.

It will also be appreciated that the inner layer 200 can be formed as a blend of two or more of the above-mentioned natural materials.

Most cotton-based personal products are formed of layers that are formed using spunbond or spunlaced fibers. However, it is possible to use thermal bonded nonwovens, which are softer but have lower resistance and strength, and trough air bonded nonwovens, which are more lofty, can also be used.

The inner layer 200 can be either hydrophilically treated or can be hydrophobically treated and in particular, the non-woven material forming the inner layer 200 can undergo a surface treatment using a treatment composition which either imparts hydrophilic properties or hydrophobic properties. Any number of different surface treatments can be used to impart increased hydrophilicity to the nonwoven fabric. For example, chemicals, such as surfactants, wetting agents and rewetting agents can increase the hydrophilic nature of the material and can make a fabric that is naturally hydrophobic into one that is hydrophilic. With respect to fibers, natural fibers tend to be hydrophilic, especially when natural oils have been removed from them. The surface treatment can be performed using any number of suitable techniques and more specifically, conventional treatments involve steps such as dipping the nonwoven in a treatment bath, coating or spraying the nonwoven with the treatment composition, and printing the nonwoven with the treatment composition.

When a nonwoven web is formed of a hydrophobic material or otherwise exhibits hydrophobic properties, it is often desirable to modify the surface of the nonwoven web using a hydrophilic surfactant to increase the wettability of the web. An external hydrophilic surfactant is typically applied to the surface of the nonwoven web. An internal hydrophilic surfactant is typically blended with the material (e.g., cellulose fibers) used to form the nonwoven web, and later migrates to the surface after the nonwoven web is formed. External and internal hydrophilic surfactants may be characterized in terms of their durability and wettability. The durability of a surfactant refers generally to its ability to withstand stresses, such as repeated washing cycles of the nonwoven fabric, without being removed from the fabric or otherwise losing its effectiveness. The wettability of a surfactant refers generally to its ability to transform a hydrophobic nonwoven web into a fabric which readily assimilates and distributes aqueous liquids. Surfactants which cause an otherwise hydrophobic nonwoven web to assimilate liquids at a relatively fast pace, with high fluid intake volumes, are referred to as faster wetting surfactants. Surfactants which cause the nonwoven web to assimilate aqueous liquids at a relatively slow pace, with low fluid intake volume, are referred to as slower wetting surfactants.

The surface treatment is thus configured to increase the hydrophilic nature of the nonwoven by reducing the surface tension of the nonwoven, reducing the contact angle with the liquid and allowing the fluid to pass. As described below, flow dynamics within the acquisition layer/absorbent core 300 prevent liquids from returning to the surface.

Figure 4A:
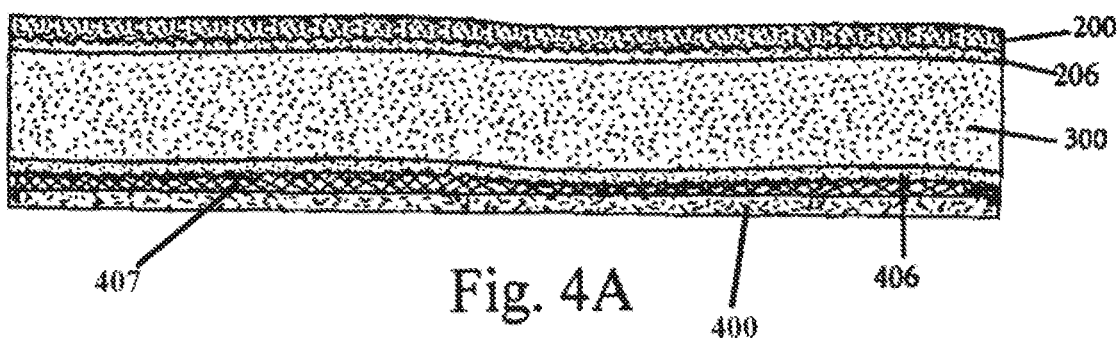
FIG. 4A is a cross-sectional view of a diaper according to a second embodiment.
Figure 4B:
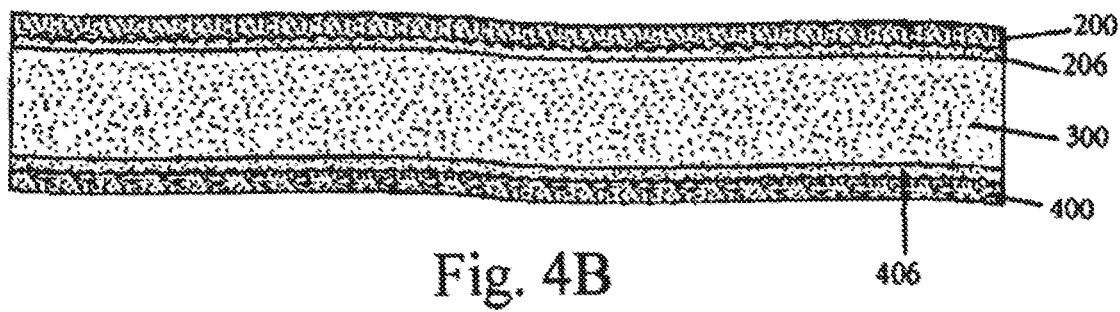
FIG. 4B is a cross-sectional view of a diaper according to a third embodiment.
Figure 5:
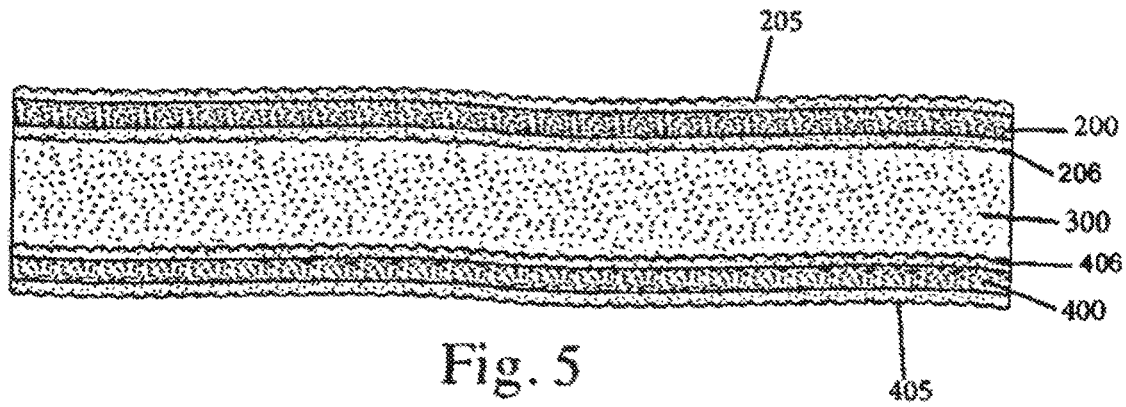
FIG. 5 is a cross-sectional view of a diaper according to a fourth embodiment.

FIG. 3 shows a surface treatment 205 applied to a top surface of the inner layer 200, i.e. the surface in contact with skin; FIGS. 4A and 4B show surface treatment 206 applied to the bottom surface of the inner layer, i.e. the surface closer to the core; and FIG. 5 shows yet another embodiment in which the surface treatment 205, 206 is applied to both the top and bottom surfaces of the inner layer 200.

It will also be understood that the surface treatment applied to the inner layer 200 can be configured as a finish that is biodegradable and imparts hydrophobic properties on one side and hydrophilic properties on the other side.

In preferred embodiments, the inner layer 200 comprises a polylaticacid (PLA) treatment 206 applied to the bottom surface, i.e. the surface closer to the core. Alternatively, the PLA is provided as a film 206 that is adhered to the bottom surface of the inner layer and/or the top surface of core 300 and can serve as an AOL as discussed further below.

Figure 7:
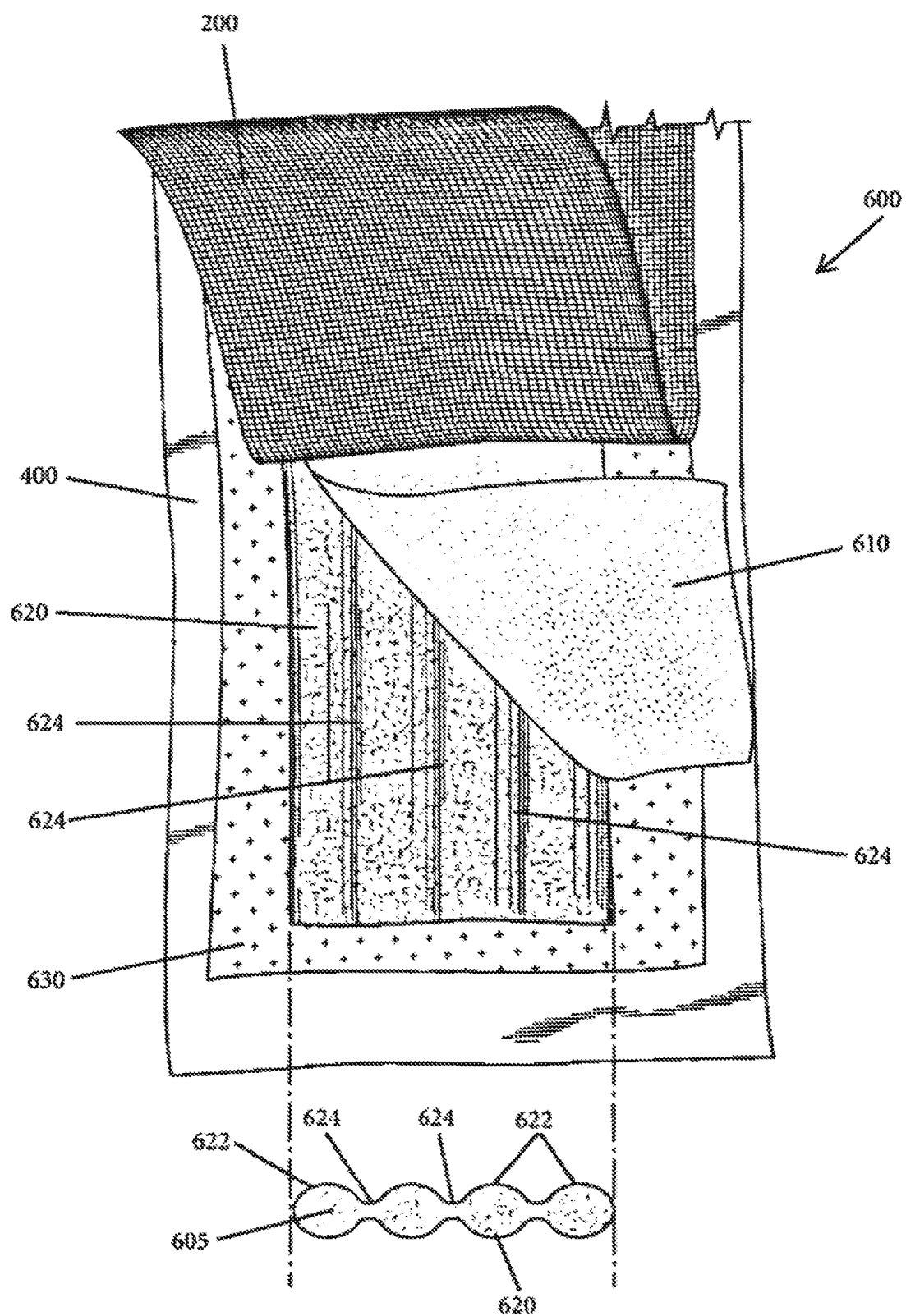
FIG. 7 is a top perspective view of a diaper according to a fifth embodiment showing the various layers/components thereof including a core wrap that can optionally be in the form of a corrugated structure.
Figure 8:
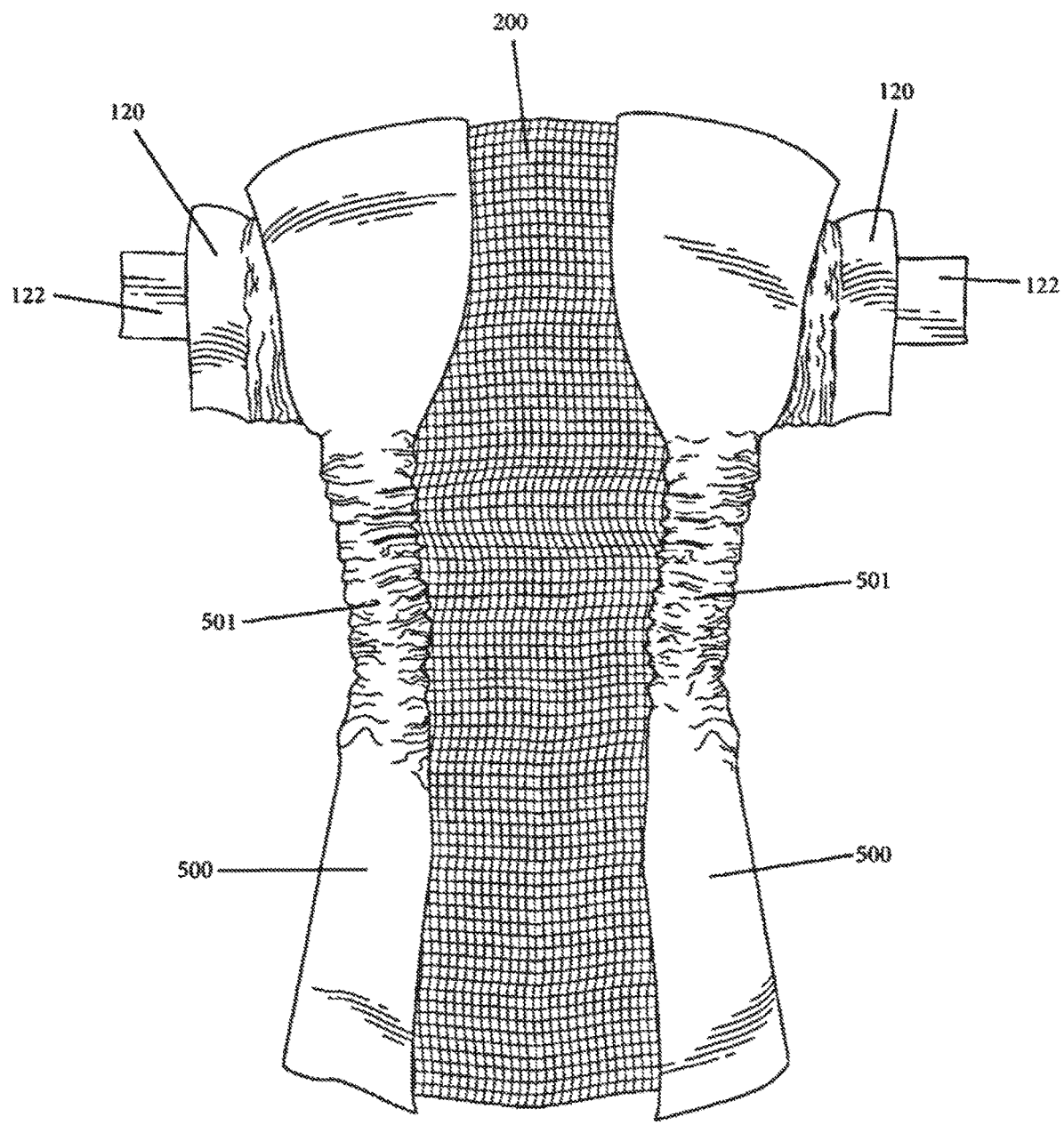
FIG. 8 is a top plan view of the diaper of FIG. 7 in an assembled state.
Figure 9:
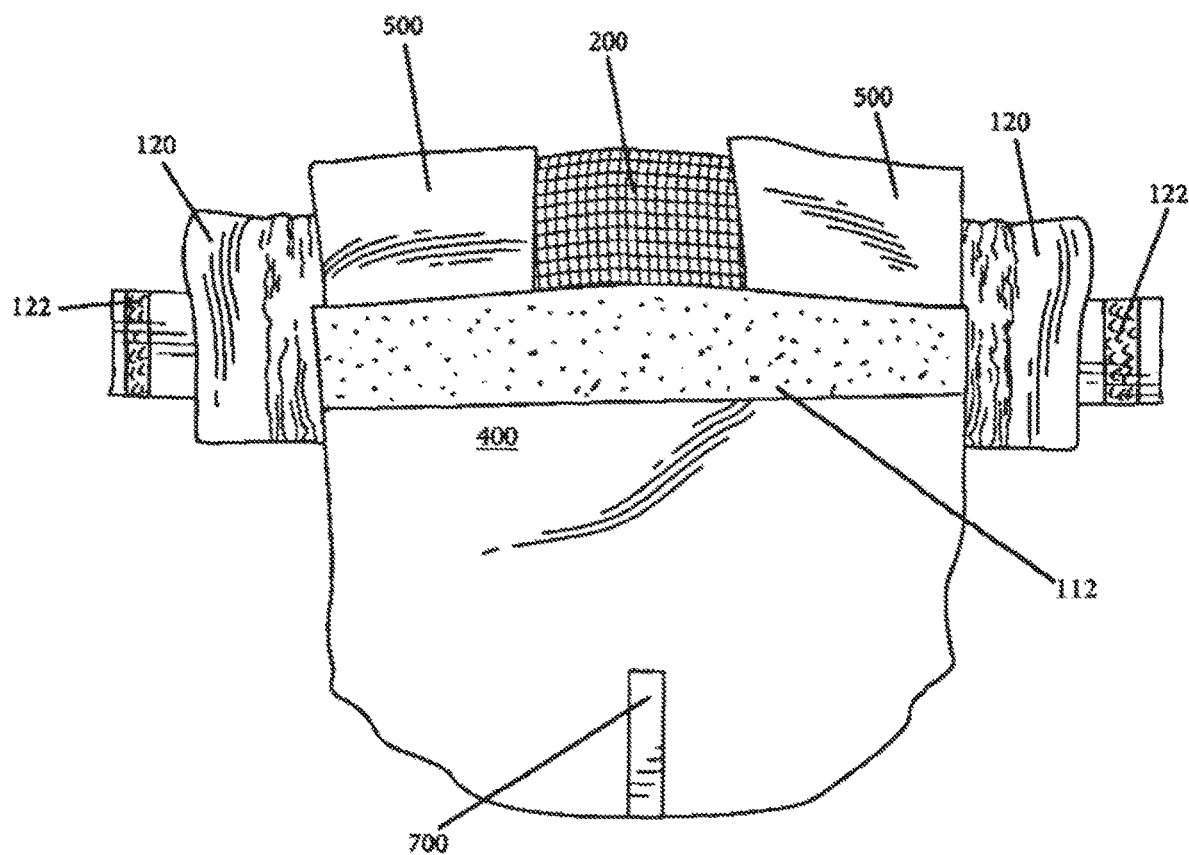
FIG. 9 is a front elevation view of the diaper of FIG. 8.

As shown in FIGS. 7-9, in certain embodiments, the inner layer comprises a plurality of openings or pores, such as those provided in a gauze-like material. These openings readily allow for the passage of fluid into an inner acquisition/distribution layer and/or absorbent core 300 so that fluid is not retained on the surface of the inner layer that touches the skin.

The nonwoven inner layer 200 can be formed by any number of suitable processes including, but not limited to, hydroentanglement, carding, air-laying, thermal treatment, or other suitable process. Pores, a dot matrix, or perforations can be created during the nonwoven formation process or can be applied to the nonwoven after formation. Any number of means can be employed to create these openings in a pre-formed nonwoven, including but not limited to air jet formation, laser formation, during extrusion or casting, or by passing a sheet through a roller mill wherein the rollers have microspikes suitable for forming pores on the sheet. Additionally, a porous sheet can be formed by incorporating microparticles of a water soluble substance and passing the sheet through a water bath after its formation. The water dissolves the microparticles so as to produce pores. In particularly preferred embodiments, the pores are structurally built during cotton sheet formation.

The openings or pores 21O in the inner layer may be any shape that allows the passage of fluid, preferably oval or round. The openings are typically between about 0.10 cm and about 0.25 cm in diameter. Preferably, the pores of the inner layer are 0.15 cm to 0.15 cm in diameter. Most preferably, the pores are 0.15 cm to 0.12 cm in diameter.

Surface Pattern for the Inner Layer

Figure 2:
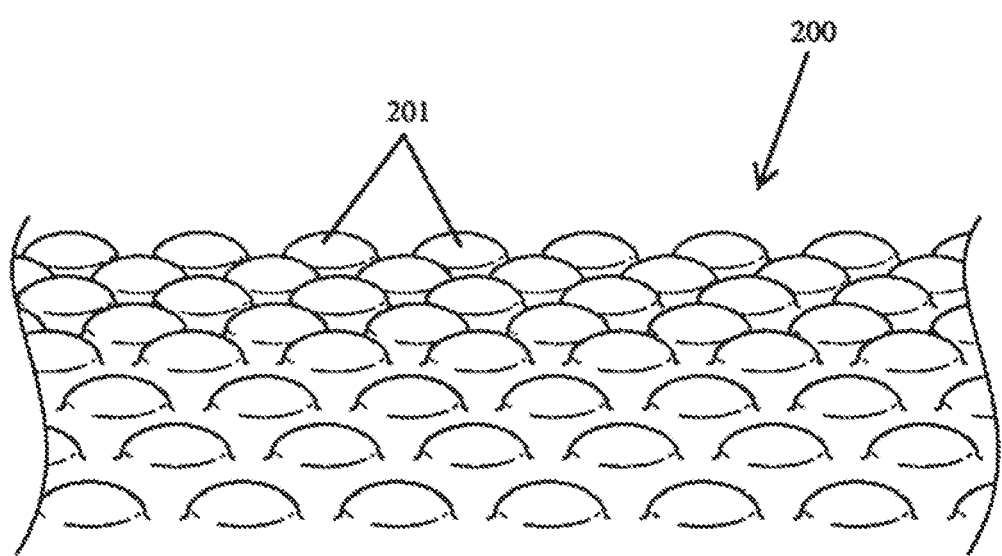
FIG. 2 is a close-up of a portion of an inner layer of the diaper according to one embodiment.

The inner layer 200 can be formed so as to have a surface pattern (surface modification) 201 that is formed as a part thereof. FIG. 2 shows one exemplary surface pattern 201 that generally has a dot matrix formation of slight protrusions across the exposed surface of the inner layer 200 in at least one region. It will be appreciated that the protrusions that define the surface pattern 201 can take any number of different forms, sizes, and shapes and thus, are not limited to the circular ones shown in FIG. 2.

The surface pattern 201 is constructed to provide fluid channeling in that fluid (e.g., urine) that is discharged onto the inner layer 200 flows into the channels/spaces that are formed between the surface modification features and away from the skin of the infant. It will therefore be appreciated that the surface pattern 201 is thus preferably provided at least in areas that are prone to receiving fluid, such as the central portion of the inner layer 200. Thus, the surface pattern 201 can be formed locally on one or more regions of the inner layer 200 or can be formed across at least substantially the entire surface of the inner layer 200.

It will also be understood that the surface pattern 201 can be formed of at least two different types of surface modification features, such as features that have different shapes and/or sizes.

Inner Acquisition/Distribution Layer (ADL) and Absorbent Core Structure

The diaper 100 can be formed to have a distinct acquisition/distribution layer and absorbent core or can be formed to have a single innermost structure that acts as the absorbent storage structure. When two or more layers are present, the acquisition/distribution layer is the layer under the inner layer (topsheet) 200 of the diaper 100. It moves liquid away from the baby's skin and distributes it more evenly across the entire diaper core for better absorbency. When the diaper 100 includes the inner layer 200 and a separate acquisition/distribution layer, along with an absorbent core structure, the acquisition/distribution layer may be formed of natural fibers, such as a nonwoven cotton material, and does not include SAP. The AOL can thus acquire a surge of fluid within the absorbent product until the superabsorbent particles (SAP) in the absorbent core structure can absorb the retained fluid out of the cellulose-based AOL and in the final storage site (absorbent core structure) containing the superabsorbent particles.

The type of personal product (absorbent article) may dictate whether or not there is a separate acquisition/distribution layer relative to the absorbent core.

The absorbent core structure is the innermost layer of the diaper and represents a storage layer (structure) that absorbs and stores the liquid acquired from the top layer(s) (e.g. inner layer and/or acquisition/distribution layer). The absorbent core structure is made up of an absorbent core (inner absorbing material) and preferably, also includes an absorbent core wrap that surrounds and contains the absorbent core. The absorbent core wrap thus encapsulates the absorbent core (inner absorbing material). FIGS. 3-5 depict embodiments in which there is only an absorbent core 300 disposed between the inner layer 200 and the back sheet 400. In this arrangement and others disclosed herein, the various layers can be bonded to one another using suitable bonding agents, such as adhesives (e.g., biodegradable glue products). As described below and shown in FIG. 7, in a different embodiment, a distinct absorbent core wrap is used to contain the material forming the absorbent core.

The absorbent core typically consists of a blend of fluff cellulose fibers and SAP (e.g., polyacrylate granules). In accordance with the present invention, the fluff cellulose material is in the form of cotton and in particular, can be in the form of loose, fluff cotton. It will be appreciated as mentioned herein, that other natural materials (e.g., bamboo, fluff pulp, etc.), described herein, can be used as the material of the AOL and/or absorbent core (inner material).

The cellulose material quickly absorbs and transfers fluid (e.g., urine) to the superabsorbent polymer material (SAP), where it is trapped. This keeps the baby's skin dry, even if he or she sits on a full diaper. Since the superabsorbent polymers absorb many times their weight in fluids, children's skin health is improved because these polymers lock moisture away where it cannot irritate skin. The severity and frequency of diaper rash has declined dramatically.

As used herein, "superabsorbent polymer" or "SAP" means any suitable hydrophilic polymer that can be mixed with fibers of the present invention. A superabsorbent polymer is a water soluble compound that has been cross-linked to render it water insoluble but still swellable to at least about 15 times its own weight in physiological saline solution. These superabsorbent materials generally fall into 3 classes, namely starch graft copolymers, cross-linked carboxymethylcellulose derivatives, and modified hydrophilic polyacrylates. Examples of absorbent polymers include hydrolyzed starch-acrylonitrile graft co-polymer, saponified acrylic acid estervinyl co-polymer, modified cross-linked polyvinyl alcohol, neutralized cross-linked polyacrylic acid, cross-linked polyacrylate salt, and carboxylated cellulose. The preferred superabsorbent materials, upon absorbing fluids, form hydrogels.

The superabsorbent polymer materials have relatively high gel volume and relatively high gel strength as measured by the shear modulus of the hydrogel. Such preferred materials also contain relatively low levels of polymeric materials which can be extracted by contact with synthetic urine. Superabsorbent polymers are well-known and are commercially available. One example is a starch graft polyacrylate hydrogel marketed under the name IM1000 (Hoechst-Celanese, Portsmouth, Va.). Other commercially available superabsorbent polymers are marketed under the trademark Sanwet (Sanyo Kasei Kogyo Kabushiki, Japan), Sumika Gel (Sumitomo Kagaku Kabushiki Haishi, Japan), Favor (Stockhausen, Garyville, La.) and the ASAP series (Chemdal, Aberdeen, Miss.). Superabsorbent particulate polymers are also described in detail in U.S. Pat. No. 4,102,340 and U.S. Pat. No. Re. 32,649. An example of a suitable SAP is surface cross-linked acrylic acid based powder such as Stockhausen 9350 or SX FAM 70 (Greensboro, N.C.). The SAP can come from any number of other sources. Other suitable SAP materials are disclosed below.

In embodiments in which the absorbent core structure includes a distinct absorbent core wrap (FIG. 7), the absorbent core wrap comprises a fabric layer (e.g., a nonwoven layer) that contains the absorbent core (inner absorbing material). As described herein, the absorbent core wrap can be formed of the biodegradable materials disclosed herein. For example, the absorbent core wrap can be in the form of a nonwoven cotton fabric or can be formed of a paper material. Additional details of the absorbent core wrap is described below.

In accordance with one embodiment of the present invention, the inner acquisition layer/absorbent core structure 300 includes a 100% cotton fluff material, such as a 100% cotton fluff blend (for the absorbent core). The thickness of the layer 300 is typically greater than the inner layer 200 since the layer 300 acts as the storage (collection) layer beneath the thinner inner layer 200. When there is a separate acquisition/distribution layer relative to the absorbent core structure, the absorbent core structure typically has a greater thickness compared to the acquisition/distribution layer.

As is known, SAPs are made from partially neutralized polyacrylic acid which is lightly cross-linked throughout small beads to form an insoluble, hydrophilic gel. In one exemplary embodiment, the SAP used in the layer 300 (as absorbent core) includes minimal (light) to no cross-linking (between the shells). The SAP is dispersed throughout the cotton fibers that form the absorbent core of the absorbent core structure 300.

In contrast to other SAP that is used in commercial products, the SAP that is particularly suited for use in the present absorbent articles comprises a 100% acrylic acid co-acrylamide with little to no cross link shell. Since the absorbent articles described herein are preferably at least substantially biodegradable, the SAP needs to have an at least substantially shell-less structure. Consequently, there is little to no cross link shell in the SAP structure. An alternative SAP structure can be a blend of acrylic acid co-acrylamide with little to no cross-link shell with an organic absorbent material, such as corn starch. The percentages of these two components in the blend can vary depending upon the particular application and in particular, the inclusion of cornstarch is preferably at a sufficient amount to encourage moisture transfer from one acrylate molecule to an adjacent acrylate molecule.

In yet another embodiment, the absorbent core (inner absorbing material) can be formed of 100% cornstarch combined with cotton lint (cotton fibers, etc.). Alternatively, the absorbent core can include 100% clay (attapulgite which is technically magnesium aluminum phyllosilicate (MgAl) 2Si401 O(OH)+4 H20).

Corrugated Shape

As described herein, to perform its function, the absorbent core structure 300 of the absorbent article (diaper 100) should be capable of intaking large volumes of fluid rapidly, with some control. In this case, the absorbent material necessarily requires a large amount of void space to take in a fluid insult (surge), but needs the appropriate structural characteristics in controlling, spreading, and retaining the fluid.

Figure 6:
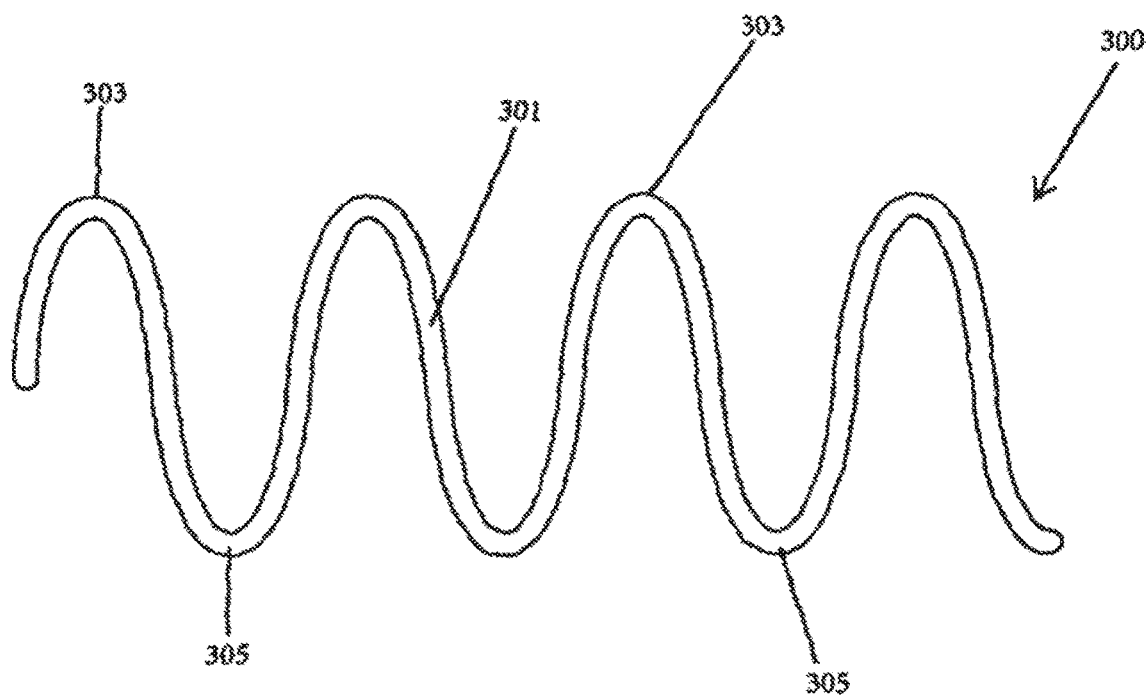
FIG. 6 is a side view of an absorbent core according to one embodiment.

In one exemplary embodiment and as shown in FIG. 6, the absorbent core structure of layer 300 is a corrugated absorbent structure 301 having a plurality of alternating peaks and valleys for use in absorbent articles. It will be appreciated that the corrugated absorbent structure 301 includes the absorbent core (inner absorbent material) and the absorbent core wrap, if present.

The corrugated absorbent core structure provides improved fluid intake due to the higher material surface area for fluid contact, void volume created by the corrugation process, a visual cue for improved fluid intake due to the improved material aesthetics, improved absorption of fluids, such as urine, menses and bowel movement due to the surface structure of material which provides "pockets" for intake, and softness and dryness due to the modified surface topology of the corrugated absorbent material providing reduced contact with the skin of the infant.

As shown in FIG. 6, the corrugated structure 301 of one embodiment comprises a plurality of alternating peaks 303 and valleys 305. The absorbency properties of the layer 300 depends on the frequency of peaks 303 and valleys 305 and can be measured as being in a range of about one per a first predetermined length of material to about one per a second predetermined length of material. The peaks 303 and valleys 305 can have any number of different shapes including rounded shaped, a triangular shape where they come to a sharp point, or a plateau shape where the peaks and valleys are relatively flat. It will also be apparent that, for some applications, a combination of shapes may be desirable. Additionally, these corrugations may be zoned in the product and localized in strategic places for different functionality. For this reason, the combination of peak frequencies and heights may be varied depending upon the effect being pursued.

To promote rapid fluid intake by the corrugated nonwoven material 301, it may be desired that the surfaces of the material or the surface of the fibers forming the material be first wetted by the liquid. Wettability of nonwoven materials or fibers thereof is known to be achievable by treating the surface thereof with surfactants. See, for example, U.S. Pat. No. 4,413,032 to Hartmann et al. and U.S. Pat. No. 5,045,387 to Schmalz.

Fluid intake benefits may be enhanced by treating the corrugated material 301 with a surfactant in a manner which produces wettability gradients within the material. A surfactant treatment can be applied to the valleys 305 of the corrugated structure 301 so as to aid in drawing fluid away from the peaks 303 (material surface), i.e. z-directed flow, of the corrugated structure 301. To further enhance the flow of fluid away from the material surface, the peaks 303 of the material may be designed to be hydrophobic. Similar functionality may also be achieved by applying a treatment to the lower surface of the corrugated structure 301. A wettability gradient for enhancement of fluid intake may also be effected by incorporating alternate raw materials, for example fluff pulps (e.g., fluff cotton) with different wettability properties, in dual or multi-layered configurations.

The use of the corrugated absorbent material of this invention is not limited to the fluid intake layers of the absorbent articles. It may also be applied to fluid distribution layer for desorption, dryness and conformance improvements.

Outer Layer (Back Sheet)

The back sheet or cover 400 is the outer layer of the diaper 100 and is constructed to prevent liquids from leaking out of the diaper 100. The back sheet 400 thus acts as a fluid barrier. In accordance with the present invention, the back sheet 400 is also formed from natural materials so as to be biodegradable and in particular, is a nonwoven structure formed from natural fibers, such as those listed herein. In one exemplary embodiment, the back sheet 400 is a nonwoven cotton structure that is constructed to provide a fluid impervious layer.

The back sheet 400 can be hydrophobically treated and in particular, the nonwoven material forming the back sheet 400 can undergo a surface treatment using a treatment composition which either imparts hydrophobic properties. Any number of different surface treatments can be used to impart increased hydrophobicity to the nonwoven fabric. For example, certain agents can increase the hydrophobic nature of the material and more particularly, materials, such as urethanes, silicones, fluorocarbons, non-fluorochemical repellants and waxes, can impart hydrophobic properties. The surface treatment can be performed using any number of suitable techniques and more specifically, conventional treatments involve steps such as dipping the nonwoven in a treatment bath, coating or spraying the nonwoven with the treatment composition, and printing the nonwoven with the treatment composition.

In some embodiments, the treatment may comprise Finish RPW dendrimer wax dispersion, Nylwick (or Nylwck) modified water dispersible polyester with ethoxylated alcohols, Aquatek Uno sulfonated nylon, Block S sulfonated nylon, WSR XF non-fluorine water repellant, NF-21 fluorinated (C6) surfactant, HC016 and/or ethox 2191. A particularly preferred form is provided as Finish Nylwck by Phoenix Chemical Company. In certain preferred embodiments, the treatment may comprise Permaseal WSR-XF C6 fluorocarbon and/or Flexiwet NF non-fluorocarbon silicon water repellant.

In certain embodiments, the hydrophobic treatment comprises dendrimer wax. In certain of those embodiments, the treatment comprises RPW.

Dendrimer waxes typically used in the invention are available in liquid form and can be applied to nonwoven materials by a number of techniques readily known in the art. An advantage of wax based treatments, and particularly dendrimer wax treatments, is that they degrade with and without oxygen. Accordingly, absorbent articles treated with these waxes are able to pass ASTM Test Method 5338.92.

The treatment is applied to the natural fibers at 100% to 200% by weight. In some embodiments, 100% to 150% by weight of the treatment is applied. In certain of those embodiments, about 125% by weight of the treatment is applied. In particularly preferred embodiments, 100% to 130% by weight of the treatment is applied to fabric. In some of those embodiments, e.g. where a dendrimer wax is used, about 120% to 125% by weight of the treatment is applied to fabric by weight. It is important that at least 100% add on by weight of the hydrophobic treatment is applied to the outer layer. It is believed that use of lower levels of such ingredients will allow the treated fabrics to retain hydrophilic characteristics, as opposed to the water resistant and water repellant properties imparted by higher concentrations of such chemicals to fabrics.

In some particularly preferred embodiments, the invention comprises applying about 125% by weight of Finish RPW dendrimer wax to a nonwoven cotton or cotton elastomeric blend. In particular, it is advantageous to apply a treatment comprising dendrimer wax or a dendrimer wax emulsion to the inside (top) surface of the outer sheet.

As used herein, the terms "percent", "%," "weight percent" and "wt %" all mean the percentage by weight of the indicated component or ingredient within the product or composition in which it is present, without dilution, unless otherwise indicated by the context in which the term is used. When the treatment is applied to a fabric, the percent", "%," "weight percent" and "wt %" refers to the amount applied to the fabric upon drying unless otherwise stated.

Treatment solutions and suspensions comprise various percentages by weight of the treatment compositions in water unless another solvent/diluent is indicated.

An external hydrophobic agent is typically applied to the surface of the nonwoven web. An internal hydrophobic agent is typically blended with the material used to form the nonwoven web, and later migrates to the surface after the nonwoven web is formed. External and internal hydrophobic agents can be characterized in terms of their durability and wettability similar to hydrophilic agents as described above.

FIG. 3 shows a surface treatment 405 applied to the bottom surface of the back sheet 400, i.e. the surface away from the core; FIG. 4A shows surface treatment 406 applied to the top surface of the back sheet, i.e. the surface closer to the core; FIG. 48 shows a surface treatment 407 applied to the top surface of the back sheet; and FIG. 5 shows yet another embodiment in which the surface treatment 405, 406 is applied to both the top and bottom surfaces of the back sheet 400.

It will therefore be appreciated that there are other combinations for the surface treatments 205, 206, 405, 406, 407 that are not shown in the figures. For example, the surface treatment 206 can be on the top surface of the nonwoven layer 300 and surface treatment 406 can be on the top surface of the nonwoven layer 400. Similarly, the surface treatment 406 can be on the bottom surface of the nonwoven layer 300 and surface treatment 405 can be on the bottom surface of the nonwoven layer 400. As another example, the surface treatment 406 can be on the bottom surface of the nonwoven layer 300 and surface treatment 406 can be on the top surface of the nonwoven layer 400. As yet another example, treatment 407 can be provided as a film that is adhered to the bottom surface of nonwoven layer 300 and also adhered to the top of treatment 406, which is applied to the top surface of layer 400.

In certain preferred embodiments, hydrophobic surface treatments 405, 406 comprise a wax, a non-fluorocarbon repellant, or a combination thereof. An example of a wax that may be used to treat the back layer is Finish RPW available from Phoenix Chemical. An example of a non-fluorocarbon repellant that may be used to hydrophobically treat the back layer is WSRXF available from Phoenix Chemical.

In some embodiments, the treatment 406 is separated from the layer 300 by a thermoplastic polyester, such as a PLA film. The film may be adhered to layer 300 and treatment 406. In other embodiments, a PLA film is adhered to the top of layer 400 and hydrophobic treatment is incorporated into or on the bottom of layer 400. Incorporation of a PLA into or on a surface of layer 400 facilitates printing of designs onto the outer layer.

Leg Cuffs, Waistband and Fasteners

As shown in FIG. 1, a rear portion 107 of the diaper 100 that defines a preferably stretchable waistband 110 includes a pair of lateral flaps 120 that each contains a refastenable fastener 122 to allow the respective lateral flap 120 to be attached to the front portion 109 of the diaper 100. The lateral flaps 120 can extend laterally and outwardly from side panels that are formed at the rear portion 107. The side panels can be formed to have a degree of stretch along with the waistband portion of the rear portion 107 that is disposed between the side panels. As described herein, the stretch portions of the rear portion 107 and any other portion of the diaper 100 can include an elastic member to provide for such stretching to accommodate different sized infants and ensure a tight fit (seal) between the diaper 100 and the infant.

The flaps 120 can be in the form of cotton tape with an adhesive layer, such as a glue. Instead of glue, other refastenable fasteners may be used, such as hook and loop mechanical fasteners or other suitable fasteners. As part of a total biodegradable absorbent article, a biodegradable glue can be used.

The front portion 109 includes a pair of tabs 140 which are placed in registration with the lateral flaps 120 when the rear portion 107 is attached to the front portion 109. To fasten the front portion 109 to the rear portion 107, the user simply removes the protective sheet that covers the adhesive layer (glue layer) to expose the adhesive and then once a proper, snug fit is achieved, the flaps 120 are attached to the front portion 109 (e.g., to the tabs 140).

In other embodiments, the flaps 120, tabs 140 and/or fasteners 122 may be comprised of polyesters or polypropylenes, preferably derived from plant based materials. In certain embodiments, the flaps 120, tabs 140 and/or fasteners 122 may be comprised of a biodegradable polymeric material such as polylactic acid or polyhydroxyalkanotes such as polydroxybutyric acid (PHB). Preferably, the fasteners 122 are comprised of PLA and comprise hook and loop structures also comprised of PLA. The hooks are placed on flaps 120 while loop structures can be placed, for instance on a strip 112, on the front portion. PLA fasteners and tabs may be adhered to the other components of the diaper by a numbers of means known in the art, such as by using a glue, thermal bonding or ultrasonic welding.

The diaper also includes a pair of leg cuffs 500 that are designed to effectively prevent leakage at the sides of the diaper 100, thereby keeping the infant's skin dry and protected. In some embodiment, the leg cuffs 500 can be constructed a set of inner standing leg cuffs and also be referred to and known as gathers. As shown in FIG. 1, the leg cuffs 500 are generally formed in the central portion of the diaper 100.

In one exemplary embodiment, each leg cuff 500 is formed of a nonwoven cotton structure with a rubber inlay to provide the desired elasticity. When the diaper 100 includes a defined elastic waistband, it too can be formed as a nonwoven cotton structure with a rubber inlay to provide elasticity thereto. Biodegradable rubber or natural rubber can be used for any elastic element that is part of the absorbent article.

It will be appreciated that the elastic structure can be formed of other materials, such as spandex and other synthetics. As mentioned herein, the elastic structures are used in cuffs, for the waist and the legs and also they can be used in lateral side panels and in tape construction. Many gasketing cuffs use spandex to provide a seal with the infant's legs.

In preferred embodiments, the leg cuffs 500 are comprised of polypropylene, ethylene, spandex or a combination thereof.

Anti-Odor Technology

In some embodiments in accordance with the present invention, the absorbent products can have anti-odor technology incorporated into the structure thereof. For example diaper 100 can include the anti-odor technology. Anti-odor technology can be built into adult incontinent products so the wearer does not have to worry about being embarrassed by the odors associated with incontinence. It will be understood that the anti-odor technology described herein is optional and the absorbent products described herein (e.g., diaper 100) can be formed without such feature.

As described herein, the anti-odor technology can be incorporated into one or more layers/structures of the diaper 100 to provide the desired anti-odor properties.

A first anti-odor technology is directed to methods to disrupt unpleasant odors through bond destruction, thereby de-volatizing molecules in nonwovens; a second anti-odor technology is directed to methods to impart non-hydrocarbon pleasant fragrances to nonwovens; and a third anti-odor technology is directed to methods to disrupt unpleasant odors in non-wovens while binding volatilized hydrocarbons using synthetic chemistry and softening agents.

Technology is used to disrupt unpleasant odors through bond destruction, thereby de-volatizing molecules in non-wovens. Bond destructing technology, such as the use of various high performance salts, can be used to disrupt unpleasant odors emanating from the absorbent product. For example, zinc salts of ricinoleic acid are highly effective active deodorizing substances. The effectiveness of zinc ricinoleate is based on the elimination of odor; it binds/degrades chemical bonds of unpleasant odorous substances in such a way that they are no longer perceivable. Yet it is also 100% natural and biodegradable as it is made from a castor oil extract. Castor oil is obtained by the cold pressing of seeds of the *Ricinus communis* plant followed by clarification of the oil by heat. Castor oil does not contain ricin because ricin is water soluble and does not dissolve in the oil obtained from the castor beans. As a result, Castor oil is approved by the Food and Drug Administration as a natural flavoring substance, as a direct food additive, and as a safe and effective stimulant laxative.

It will be appreciated that the aforementioned substance can be incorporated into one of the layers of the diaper 100 and can be incorporated into more than one layer of the diaper 100. In one exemplary embodiment, the anti-odor technology is incorporated into the acquisition layer/absorbent core 300 by treating such material using conventional processes including those mentioned herein with respect to applying the surface treatments 305, 405.

Other options include crown ether, which is an odor-absorbing molecule, but this substance is synthetic and not biodegradable. Certain clays can absorb odor, as can baking soda under certain conditions. However, zinc ricinoleate (as other similar metal salts) offer better performance than these alternatives since in a damp environment, zinc ricinoleate is activated and absorbs odor more effectively than clays and baking sodas, which don't perform well when wet.

Another alternative is a cyclodextrin, which is currently used as a sprayable odor absorber; however, it can be designed to be applied to at least a portion of the diaper 100. Cyclodextrins work well; however, they are non-selective, unlike zinc ricinoleate, which prefers to damage nitrogen and sulfate bonds, and thus don't allow for any other volatile fragrances to be applied or incorporated into the final products.

The cyclodextrin molecule traps and binds volatilized hydrocarbons within its structural ring, retaining malodorous molecules, which reduces their volatility and thus the perception of their scent. It also binds other pleasant odors as well. Thus, in an alternative embodiment, cyclodextrin can be directly applied during manufacture of the various layers of the end use product (e.g., diaper 100), so no after sprays are necessary.

An alternative anti-odor technology involves adding non-hydrocarbon based fragrances into nonwovens to impart malodor control non-selectively based on hydrocarbon devolatilization and yet still offer fragrances that are not volatile hydrocarbon based, or are too large to bind, such as lavender or synthetic fresh and clean scents, synthetic powder scents, etc. These scents are still volatile enough to be detected yet they are synthetically created to not be trapped in structure rings of cyclodextrin molecules or they are simply too large of a molecule themselves for the cyclodextrins to bind and deactivate.

A third method is focused more on the application of fragrance to mask unpleasant odor, or simply create a more pleasant odor than no technology, with softening agents or compounds applied like softening agents. The softening compounds differ in affinity to different materials. Some are better for cellulose-based fibers (e.g., cotton), others have higher affinity to hydrophobic materials like nylon, polyethylene terephthalate, polyacrylonitrile, etc.

Cyclodextrins, clays, and various fabric softeners are used as sprays or for application during/after washing/drying durable fabrics (not one time use nonwovens). They are available as solutions and solids, sometimes impregnated in dryer sheets to impart fragrance to mask mal odor or add more pleasant odors to various surfaces. Cyclodextrins and clays are discussed in more detail above.

Silicone-based compounds such as polydimethylsiloxane comprise the new softeners which work by lubricating the fibers. Derivatives with amine- or amide-containing functional groups are used as well. These groups help the softeners bind better to fabrics.

As the softeners themselves are often hydrophobic, they are commonly occurring in the form of an emulsion. In the early formulations, soaps were used as emulsifiers. The emulsions are usually opaque, milky fluids. However, there are also microemulsions where the droplets of the hydrophobic phase are substantially smaller. The advantage of microemulsions is in the increased ability of the smaller particles to penetrate into the fibers and better stability. A mixture of cationic and nonionic surfactants is often used as an emulsifier. Another approach is using a polymeric network, an emulsion polymer.

Cationic Fabric Softeners

In the 1950s, distearyldimethylammonium chloride (DHTDMAC), was introduced as a fabric softener initially to counteract the harsh feel that the machine washing imparted to diapers. This compound was discontinued because the cation biodegrades very slowly. Contemporary fabric softeners tend to be based on salts of quaternary ammonium cations. Characteristically, the cations contain one or two long alkyl chains derived from fatty acids. Other cationic compounds can be derived from imidazolium, substituted amine salts, or quaternary alkoxy ammonium salts.

In an exemplary embodiment, distearyldimethylammonium chloride, a fabric softener with low biodegradability, may be used.

Anionic Fabric Softeners

Anionic softeners and antistatic agents can be, for example, salts of monoesters and diesters of phosphoric acid and the fatty alcohols. These are often used together with the conventional cationic softeners. Cationic softeners are incompatible with anionic surfactants used in detergents because they combine with them to form a solid precipitate. So, they must instead be added during the rinse cycle. Anionic softeners can be combined with anionic surfactants directly. Other anionic softeners can be based on smectite clays. Some compounds, such as ethoxylated phosphate esters, have softening, antistatic, and surfactant properties.

Zinc ricinoleate is a particularly preferred anionic softener. Zinc ricinoleate [Zn(Ri)2] is widely used in surfactant and detergent mixtures for the adsorption of odor-active compounds. The mechanism of this process is not fully known, however it reacts very well with nitrogen and some sulfate containing compounds. There are published studies available, one study is found at: Journal of Surfactants and Detergents, July 2000, Volume 3, Issue 3, pp 335-343, Mechanism of the odor-adsorption effect of zinc ricinoleate. A molecular dynamics computer simulation H. Kuhn, F. Moiier, J. Peggau, R. Zekorn, the contents of which are hereby incorporated by reference in its entirety.

Zinc ricinoleate or other cyclodextrins, salts, softening agents or derivatives can be applied by dip, pad, or spray bar to nonwovens during the manufacturing stage after fabric formation but before take-up. Typically, application is either just before, in a mid-stage, or just after the dryers of the machinery. It is preferable to get as much possible uptake to have the least interference with other chemistries as possible. In order to prevent molding of the fabric during storage and transport, it is preferable that the fabric is fully formed and this technology dried before rolls are created and bagged for storage.

In accordance with one exemplary embodiment of the present invention, a deodorizing composition for use with the absorbent articles described herein has the following formulation:

between 0.1% and 10% of a zinc, copper, silver or aluminum salt, most preferably zinc rincinoleate; and/or a binder consisting of individual components or a combination of the following; ethoxylated alcohols, ethoxylated glycols, ethoxylated oils, polymers or co-polymers of acrylic acid (including methacrylic acid); and/or coupling agents consisting of individual components or a combination of the following; ethoxylated alcohols, ethoxylated glycols, ethoxylated oils polymers or copolymers of acrylic acid (including methacrylic acid), and/or drying agents consisting of any primary, secondary, or tertiary alcohol or solvent (including any ketone).

The above anti-odor composition can be carried in either an aqueous or solvent based system.

In one preferred embodiment, the deodorizing composition has the following formulation (listed by weight percentages):

| Ingredient | % w/w |
| --- | --- |
| Zinc Rincinoleate (deodorant) | 2.00 |
| Cetyl Alcohol (thickener, emollient) | 2.50 |
| Glyceryl stearate and PEG-100 stearate - Acid-Stable (emulsifier) | 4.00 |
| Triglyceride (emollient) | 4.00 |
| Ceteareth-20 (emulsifier) | 2.00 |
| Polyglyceryl Oleate (emulsifier) | 1.00 |
| distilled water | 76.00 |
| citric acid | 0.01 |
| ethyl alcohol | 9.00 |

FIGS. 7-9 illustrate another absorbent article (e.g., a diaper) 600 in accordance with the present invention. The diaper 600 includes many, if not all, of the layers described hereinbefore with respect to other absorbent article products. As with the previous embodiments, the diaper 600 is a biodegradable product and more specifically and preferably, is at least substantially 100% biodegradable.

It will be appreciated that while the construction 600 is described and shown as being a diaper, the construction 600 can be implemented in other absorbable products, such as those described herein.

Inner Layer

Diaper 600 includes inner layer (top sheet) 200. In FIG. 7, the inner layer 200 is shown partially folded back in order to expose and illustrate the other layers of the diaper 600. The inner layer 200 can be formed of any of the materials disclosed hereinbefore. Thus, the inner layer 200 is formed a biodegradable material and in the illustrated embodiment, the inner layer 200 is formed of cotton (e.g., a nonwoven cotton).

As mentioned above, a surface treatment can be applied to the inner layer 200 to impart hydrophobicity or hydrophilicity. In certain preferred embodiments, the inner layer 200 is hydrophobic.

As shown in FIG. 7, the inner layer 200 can be in the form of a sheet and more particularly, can have a gauze like structure (e.g. cotton gauze structure). As is known, a gauze is a thin fabric with a loose open weave. The term "gauze" actually refers to a weave structure in which the weft yarns are arranged in pairs and are crossed before and after each warp yarn, thereby keeping the weft firmly in place. This construction allows fluid to rapidly travel away from baby's skin and into the absorbent core 300.

The inner layer 200 is thus a soft, comfortable barrier layer formed of a biodegradable material.

ADL Construction

Below the inner layer 200 in FIG. 7 is an acquisition distribution layer (AOL) 610. As mentioned previously, the AOL is an optional component (layer) in the diaper 600 and therefore, while the diaper 600 is shown as including AOL 610, it will be appreciated that such layer can be eliminated from the diaper 600. The AOL 610 can be formed of any number of different materials that perform the intended function (fluid acquisition and distribution to another layer (i.e., the absorbent core)) including those mentioned herein before and in one embodiment, the AOL 610 is in the form a biodegradable sheet, such as one formed of a natural material. The AOL 610 can thus be in the form of cotton fabric material (e.g., a nonwoven cotton sheet) and/or PLA. As previously mentioned, the AOL of a conventional diaper has a synthetic construction in that it is formed of polypropylene/polyethylene (PP/PE) and is thus not biodegradable. In preferred embodiments, the AOL is comprised of PLA.

In certain embodiments, the footprint of the inner layer 200 is preferably greater than the footprint of the AOL 610 as shown. As a result, when the inner layer 200 is laid over the AOL 610, the inner layer 200 completely covers and extends outwardly beyond the peripheral edges of the AOL 610 (i.e., the inner layer 200 overhangs the edges of the AOL 610).

In other preferred embodiments of a diaper, the footprint of the inner layer is coextensive with the footprint of the AOL 610. In these embodiments, the AOL expands across the width of the diaper from one leg cuff 500 to the other. This construction keeps any SAP from leaking into the diaper or onto baby's skin if the 620 core wrap were to break.

In preferred embodiments, the inner layer is adhered to the AOL with an adhesive, such as a glue. It is preferred that the adhesive is only applied to the peripheral edges of the AOL. Over application of adhesive to either the AOL or inner layer can negatively affect the movement of fluid into the AOL/core and impart a feeling of wetness against the skin.

Absorbent Core Structure

The diaper 600 includes an absorbent core structure which is formed at least of an absorbent core 605 and optionally, also includes an absorbent core wrap 620 that encapsulates and contains the material(s) forming the absorbent core 605. As described herein, the absorbent core wrap 620 can be shaped so as to impart a shape to the overall structure. The absorbent core structure is located adjacent either the inner layer 200 or the AOL 610 if present.

The absorbent core wrap 620 can be formed of any number of different materials and can be provided in any number of different shapes. Suitable biodegradable materials have been discussed hereinbefore. For example, the absorbent core wrap 620 can be formed of natural fibers, such as, cotton or can be formed of other natural fibrous materials, such as wood pulp or the like. Thus, according to one exemplary embodiment, the absorbent core wrap 620 can be formed of cotton and can be formed so as to define a hollow interior space that receives the absorbent core 605, namely, the SAP and pulp. The absorbent core wrap 620 can thus be in the form of a wrap or envelope structure that contains the SAP and pulp. Exemplary shapes of the absorbent core wrap 620 are discussed below.

In one embodiment, the absorbent core wrap 620 is treated with a hydrophilic agent, such as those described herein, so as to increase the hydrophilicity of the wrap 620 and allow the wrap 620 to push the moisture (fluid) to the inner material (absorbent core) contained therein (which by nature is very hydrophilic in nature).

More specifically and according to one embodiment, the absorbent core wrap 620 can be a cotton non-woven and can optionally include a polyvinyl acetate (PVA) binder sprayed with a wicking agent. Use of cotton as the absorbent core 620 provides a thicker absorbent core structure which allows for the elimination of the optional AOL material. The absorbent core wrap 620 is the mechanism by which the SAP and pulp are contained and transfer moisture quickly to those membranes (the SAP and pulp) which forms the absorbent core 605.

In some embodiments, the core is adhered to the AOL and/or the inner layer with an adhesive, such as a glue. It is preferred that the adhesive is only applied to the peripheral edges of the core. Over application of adhesive to either the core, AOL or inner layer can negatively affect the movement of fluid into the AOL/core and impart the feeling of wetness against the skin.

SAP

As mentioned above, the absorbent core wrap 620 can take any number of different shapes. For example, it can be similar to a pillow case (with closed ends) in that it has a top layer and an opposing bottom layer that are joined so as to create a hollow interior for receiving the internal components, namely and for example, SAP and pulp. Alternatively, the absorbent core wrap 620 can have the construction shown in FIG. 7 and more specifically, the absorbent core wrap 620 can be a corrugated shaped core with a hollow interior that receives the internal components. The corrugated core wrap 620 shown in FIG. 7 is defined by a series of peaks 622 and alternating valleys 624. The valleys define channels for moving moisture quickly. The channels and valleys are arranged longitudinally along the length of the absorbent core wrap 620. It will be appreciated that the size and number of channels can vary.

Alternatively, the absorbent core wrap 620 can be formed from a paper material (cellulose pulp). The paper absorbent core wrap 620 offers excellent performance and does not require any chemical treatment. Any number of different paper based materials can be used so long as they are suitable for the intended application. When the absorbent core wrap 620 is formed of paper, the hollow interior defined therein is still filled with other absorbent materials, such as those describes above (e.g., SAP and pulp). It will be appreciated that this alternative absorbent core wrap 620 is likewise biodegradable.

As mentioned above, one of the components that is disposed within the absorbent core wrap 620 and makes up the absorbent core 605 is SAP. The SAP that is used in combination with absorbent core wrap 620 can be any of the SAP materials discussed herein. For example, the SAP can be in the form of 100% acrylic acid coacrylamide with little to no shell. As is known, the shell of the SAP constitutes more tightly crosslinked polymer relative to the center core of the shell.

The reduction or elimination of the SAP shell provides for a biodegradable SAP and allows for the entire diaper 600 to be environmentally friendly (i.e., biodegradable).

In an alternative embodiment, the SAP can be in the form of acrylic acid coacrylamide (with little to no shell) combined with another biodegradable material, such as starch from corn, potato, yams or other starch-rich plants. For example, the SAP can be a mixture of acrylic acid co-acrylamide (with little to no shell) with corn starch. The percentage of each component can vary depending upon the application and also based on other considerations. In general and according to one embodiment, each component can be present in an amount from 10% to 90% of the overall total (by weight), with the weight percentages of all of the components adding up to 100% (however, this is merely an exemplary embodiment and others are equally possible including those outside this range).

In yet another embodiment, the absorbent core 605 can eliminate the use of SAP as a part thereof and instead can be based on a 100% biodegradable material, such as starch from corn, potato, yams or other starch-rich plants. For example, 100% corn starch can be used as the absorbent core 605 in the interior of the absorbent core wrap 620. The corn starch can also be mixed with another different biodegradable material, such as cotton lint or other natural fibrous material.

In yet a further embodiment, the absorbent core 605 can contain 100% clay (attapulgite which is technically magnesium aluminum phyllosilicate $(MgAl)2Si4O10(OH)+4 H20$). The clay is similarly disposed within the hollow interior of the absorbent core 605.

As will be understood, when the absorbent core 605 consists of a natural material, such as pulp/fluff, and SAP, the pulp/fluff serves to hold and space out the SAP so that the SAP is not all in one loose mass at the lowest point in the absorbent article. By distributing the SAP across the absorbent article structure, the absorbency of the SAP is optimized.

Film Layer

Optionally, a film 630 can be provided and disposed adjacent the absorbent core structure on the rear side thereof. The film 630 is thus disposed in contact with the absorbent core structure (e.g., the wrap 620 when present). As shown in FIG. 7, the film 630 can have a larger footprint than the absorbent core structure. The film 630 thus extends completely around the absorbent core structure (extends outwardly from the peripheral edges of the absorbent core structure). In one embodiment, the footprint of the film 630 is about the same as the footprint of the absorbent core structure.

Traditional films used in conventional diaper constructions are formed typically of nonwoven polypropylene/polyethylene (PP/PE). As with the other components of diaper 600, the film 630 is formed of a biodegradable material. For example, the film 630 can be formed of a polylactic acid (PLA) or polylactide biodegradable thermoplastic material. Incorporation of a PLA film 630 facilitates printing of designs onto the back sheet 400.

In preferred embodiments, the film is adhered to the outer layer with an adhesive, such as a glue, or by thermal or ultrasonic methods. It is preferred that the film is only adhered to other layers at the peripheral edges of the film. Over application of adhesive or bonding means can negatively affect the movement of fluid into the AOL/core.

Once again, the film 630, which acts as a barrier, is optional.

Leg Cuffs

The diaper also includes a pair of leg cuffs 500 that are designed to effectively prevent leakage at the sides of the diaper 600, thereby keeping the infant's skin dry and protected. As with the other components, the leg cuffs 500 are formed of a biodegradable material. Any number of biodegradable materials, including those described herein, can be used to form the leg cuffs 500. For example, the leg cuffs 500 can be formed of cotton (nonwoven) or other natural material.

Each leg cuff 500 has an associated elastic element 501 to ensure improved fit around the legs and prevent leakage. The elastic element 501 can be formed of a suitable material, such as a natural rubber, biodegradable rubber, or a biodegradable polymer. As in traditional diapers, the elastic element 501 extends along a length of the leg cuff 500 and creates a cuff gather in a central location of the cuff 500 as shown in FIG. 8.

Back Sheet/Cover

As with the previous diapers, the diaper 600 includes back sheet or cover 400 which represents the outer layer of the diaper 100 and is constructed to prevent liquids from leaking out of the diaper 100. The back sheet 400 thus acts as an outer cover. As shown in FIG. 7, the back sheet 400 typically has a footprint that is greater than those of the other components including the inner layer 200.

As mentioned, it is preferable that the other layers of diaper 600 are bonded or adhered to each other and/or the back sheet at the peripheral edges the respective layers. Over application of adhesive or bonding means can negatively affect the movement of fluid into the AOL/core.

In accordance with the present invention, the back sheet 400 is also formed from natural materials and in particular, is a nonwoven structure formed from natural fibers, such as those listed herein or other suitable biodegradable materials. The inner layer 200 and the back sheet 400 can be formed of the same material. In one exemplary embodiment, the back sheet 400 is a nonwoven cotton structure that is constructed to provide a fluid impervious layer.

The back sheet 400 can be hydrophobically treated and in particular, the nonwoven material forming the back sheet 400 can undergo a surface treatment using a treatment composition which either imparts hydrophobic properties. Any number of different surface treatments can be used to impart increased hydrophobicity to the nonwoven fabric. For example, certain agents can increase the hydrophobic nature of the material and more particularly, materials, such as urethanes, silicones, fluorocarbons, non-fluorochemical repellants and waxes, can impart hydrophobic properties. The surface treatment can be performed using any number of suitable techniques and more specifically, conventional treatments involve steps such as dipping the nonwoven in a treatment bath, coating or spraying the nonwoven with the treatment composition, and printing the nonwoven with the treatment composition.

At least in some embodiments, back sheet 400 can be used by itself with no other barrier films and/or surface treatments.

Other details concerning the back sheet 400 are discussed herein with reference to other diaper constructions, such as diaper 100.

As shown in FIG. 9, the diaper 600 can contain a wetness indicator 700. Wetness indicter 700 is a feature that reacts to exposure of liquid as a way to discourage the wearer to urinate in the training pants, or as an indicator for parents that a diaper needs changing. The wetness indicator 700 can be of a type which "fades when wet" meaning that the wetness indicator 700 fades as a reaction to liquid, specifically urine. The wetness indicator 700 is shown as being a stripe; however, it will be appreciated that this is merely an exemplary graphic and others are equally possible.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A disposable absorbent article comprising:
a non-woven inner layer consisting of natural fibers;
a hydrophobic non-woven outer layer, the hydrophobic non-woven outer layer consisting of:
   natural fibers treated with an internal hydrophobic agent; and
   an external hydrophobic surface treatment applied to a surface of the non-woven outer layer, the external hydrophobic surface treatment selected from the group consisting of waxes, urethanes, silicones, fluorocarbons, non-fluorochemical repellants applied to at least one surface thereof;
a core comprising natural fibers or fibrous material positioned between the inner layer and the outer layer, and
an acquisition/distribution layer comprised of polylactic acid between the non-woven inner layer and the core.

2. The absorbent article of claim 1, wherein the absorbent article is selected from the group consisting of: diapers, nappies, absorbent underpants, training pants, adult incontinence products, pet incontinence products, feminine hygiene products, wound dressings, and breast pads.

3. The absorbent article of claim 1, wherein the core comprises polyacrylate superabsorbent particles (SAP).

4. The absorbent article of claim 1, wherein the core comprises a corrugated structure defined by a plurality of peaks and valleys.

5. The absorbent article of claim 1, wherein the core comprises a non-woven wrap surrounding loose fibers.

6. The absorbent article of claim 1, wherein the outer layer treatment comprises dendrimer wax.

7. The absorbent article of claim 1, wherein the treatment is applied to the top surface of the outer layer.

8. The absorbent article of claim 1, wherein the inner layer includes a plurality of pores.

9. The absorbent article of claim 1, wherein at least one layer includes a deodorizing composition comprising between about 0.1% and about 10% of a zinc, copper, silver or aluminum salt.

10. The absorbent article of claim 9, comprising about 0.1% and about 10% zinc rincinoleate.

11. The absorbent article of claim 10, wherein the deodorizing composition further comprises:
at least one compound selected from the group consisting of ethoxylated alcohols, ethoxylated glycols, ethoxylated oils, polymers or co polymers of acrylic acid and combinations thereof; and
at least one drying agent selected from the group consisting of primary, secondary, and tertiary alcohols and combinations thereof.

12. A biodegradable diaper comprising:
a non-woven inner layer comprising cotton;
a hydrophobic non-woven outer layer, the hydrophobic non-woven outer layer comprising:
   cotton treated with an internal hydrophobic agent, wherein the internal hydrophobic agent is a dendrimer wax; and
   an external hydrophobic surface treatment applied to a surface of the non-woven outer layer, the external hydrophobic surface treatment selected from the group consisting of waxes, urethanes, silicones, fluorocarbons, and non-fluorochemical repellants and combinations thereof; and
an absorbent core comprising cotton and polyacrylate superabsorbent particles positioned between the inner layer and the outer layer.

13. The diaper of claim 12, wherein the inner layer comprises a plurality of pores.

14. The diaper of claim 12, further comprising a polylactic acid film disposed between at least one of the core and the outer layer or the core and the inner layer.

15. The diaper of claim 12, wherein the treatment is applied to the outer layer at 100% to 200% by weight add on.

16. The diaper of claim 12, wherein the treatment is applied only to the top surface of the outer layer.

17. The diaper of claim 12, further comprising a pair of lateral flaps extending from a rear portion of the outer layer, said flaps including polylactic acid fasteners capable of affixing the flaps to a front portion of the outer layer.

18. The diaper of claim 12, wherein the diaper passes at least one of ASTM Test Method 05511-12, ASTM Test Method 5338-15, and ISO CD Test Method 14855-1:2012.

19. A disposable absorbent article, comprising:
a non-woven inner layer comprising natural fibers;

a hydrophobic non-woven outer layer, the hydrophobic non-woven outer layer comprising:
  natural fibers treated with an internal hydrophobic agent; and
  an external hydrophobic surface treatment applied to a surface of the non-woven outer layer, the external hydrophobic surface treatment selected from the group consisting of waxes, urethanes, silicones, fluorocarbons, non fluorochemical repellants applied to at least one surface thereof; and
a core comprising natural fibers or fibrous material positioned between the non-woven inner layer and the non-woven outer layer, the core comprising:
  a corrugated absorbent structure of absorbent material comprising natural fibers or fibrous material, the corrugated absorbent structure having a plurality of alternating peaks and valleys, the plurality of alternating peaks and valleys providing a fluid retainment space in the core,
wherein the treatment is applied to the non-woven outer layer at 100% to 200% by weight add on.

20. The disposable absorbent article according to claim 19, wherein the internal hydrophobic agent is a dendrimer wax.

* * * * *